(12) United States Patent
Miura et al.

(10) Patent No.: US 8,241,589 B2
(45) Date of Patent: Aug. 14, 2012

(54) FLOW CELL

(75) Inventors: Toru Miura, Kanagawa (JP); Tsutomu Horiuchi, Kanagawa (JP); Yuzuru Iwasaki, Kanagawa (JP); Michiko Seyama, Kanagawa (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 39 days.

(21) Appl. No.: 12/864,222

(22) PCT Filed: Jan. 30, 2009

(86) PCT No.: PCT/JP2009/051588
§ 371 (c)(1),
(2), (4) Date: Jul. 22, 2010

(87) PCT Pub. No.: WO2009/096527
PCT Pub. Date: Aug. 6, 2009

(65) Prior Publication Data
US 2010/0296972 A1 Nov. 25, 2010

(30) Foreign Application Priority Data
Feb. 1, 2008 (JP) .................................. 2008-022594

(51) Int. Cl.
*G01N 21/05* (2006.01)
*G01N 21/11* (2006.01)
(52) U.S. Cl. ..... 422/507; 417/572; 417/544; 435/283.1; 137/565.01; 137/833; 436/180
(58) Field of Classification Search .......................... None
See application file for complete search history.

(56) References Cited

U.S. PATENT DOCUMENTS
6,637,463 B1  10/2003  Lei et al.
(Continued)

FOREIGN PATENT DOCUMENTS
EP   1 685 900 A1   8/2006
(Continued)

OTHER PUBLICATIONS
Analytical Chemistry, vol. 77, No. 24, Dec. 15, 2005, pp. 7901-7907.
(Continued)

*Primary Examiner* — In Suk Bullock
*Assistant Examiner* — Timothy G Kingan
(74) *Attorney, Agent, or Firm* — Blakely, Sokoloff, Taylor & Zafman

(57) ABSTRACT

A measurement fluidic channel (17) is formed at almost the center of a flow cell (1). In general, the measurement region of a measurement apparatus is set to focus on almost the center of a measurement chip. When the flow cell (1) is mounted in the measurement apparatus, the focus of the measurement region is positioned just above the measurement fluidic channel (17). The measurement apparatus can more reliably measure a sample solution flowing through the measurement fluidic channel (17). A suction pump (18) is formed in regions around the measurement fluidic channel (17). When the flow cell has the same planar shape as a conventional one, the amount of sample solution which can be supplied can be increased, compared to a conventional structure in which components are formed in line. The time during which a sample solution flows through the fluidic channel can be prolonged, the amount of sample solution can be increased, and the measurement time can also be prolonged. A sample solution flowing through the fluidic channel can be measured more reliably.

9 Claims, 10 Drawing Sheets

5

U.S. PATENT DOCUMENTS

| | | | |
|---|---|---|---|
| 2005/0147531 A1* | 7/2005 | Buechler | 422/58 |
| 2006/0043284 A1 | 3/2006 | Baba et al. | |
| 2008/0003572 A1 | 1/2008 | Delamarche et al. | |
| 2008/0257754 A1* | 10/2008 | Pugia et al. | 205/792 |

FOREIGN PATENT DOCUMENTS

| | | |
|---|---|---|
| JP | H07-036017 B | 4/1995 |
| JP | 2000-329766 A | 11/2000 |
| JP | 2004-077305 A | 3/2004 |
| JP | 2006-225197 A | 8/2006 |
| JP | 2007-530938 A | 11/2007 |
| WO | WO 2004/051228 A1 | 6/2004 |
| WO | WO 2007/149042 A1 | 12/2007 |

OTHER PUBLICATIONS

Zimmermann et al., "Capillary pumps for autonomous capillary systems", The Royal Society of Chemistry 2007, Lab Chip, pp. 119-125.

Horiuchi et al., "Passive-fluidic device using integrated capillary tubes for SPR measurement without external pump", Extended Abstracts (The 55th Spring Meeting, 2008); The Japan Society of Applied Physics and Related Societies, No. 3, Mar. 27, 2008, p. 1353.

* cited by examiner

FLOW CELL

This is a non-provisional application claiming the benefit of international application number PCT/JP2009/051588 filed Jan. 30, 2009.

TECHNICAL FIELD

The present invention relates to a flow cell having a predetermined fluidic channel used for measurement by a measurement apparatus, and a pump for supplying a sample solution to the fluidic channel.

BACKGROUND ART

Measurement using a sophisticated biomolecule identification function such as an antigen-antibody reaction and binding of a DNA fragment (DNA probe) to DNA is becoming an important technique in clinical testing, measurement in the field of biochemistry, and measurement for environmental pollutants. Examples of the measurement are micro-TAS (Total Analysis Systems), micro combinatorial chemistry, chemical IC, chemical sensor, biosensor, microanalysis, electrochemical analysis, QCM measurement, SPR measurement, and ATR measurement. In the field of measurement, the amount of sample solution to be measured is often very small.

In this measurement, a small amount of sample solution is directly transferred to a detecting portion to measure it with high sensitivity and high efficiency without decreasing the concentration of the analyte. As a technique for transferring a small amount of sample solution, a several hundred μm wide-fluidic channel is formed on a substrate, and a solution is transferred by an external pressure by a syringe pump or the like. Alternatively, a solution is transferred by electrostatic force, by electrowetting, by changing the volume or generating bubbles upon heating, or by using an electroosmotic flow.

To transfer a small amount of sample solution by these methods, it is necessary to form a microchannel as a fluidic channel on a substrate (chip), and arrange other components on this substrate. It is not easy to fabricate this structure. Transferring a sample solution by an external pressure requires components such as a pump and tube in addition to a chip which forms a fluidic channel. A sample solution is wasted on the transfer path including the tube, which exerts a limitation on decreasing the amount of sample solution.

As a method of analyzing a small amount of sample solution, paper chromatography analysis using filter paper has conventionally been known. For example, improved immunochromatography and immunoconcentration have been proposed as simple, low-cost means for measurement of biological substances (Japanese Patent Publication No. 7-036017, and Japanese Patent Laid-Open No. 2000-329766). There is also proposed a measurement chip in which filter paper is arranged in a fluidic channel formed in a plastic structure (Amal. Chem. 2005, 77. 7901-7907). However, these paper chromatography methods have limitations in the shape of the fluidic channel and the like, and cannot perform complicated chemical analysis.

Under the circumstance, it is recently proposed to form, on or in a substrate by a microfabrication technique, regions serving as a fluidic channel and pump for transferring a sample solution by capillary action (Martin Zimmermann, Heinz Schmid, Patrick Hunziker and Emmanuel Delamarche, "Capillary pumps for autonomous capillary systems", The Royal Society of Chemistry 2007, Lab Chip, 2007, 7, 119-125, First published as an Advance Article on the web 17 Oct. 2006). In a measurement chip fabricated by this technique, an inlet port for introducing a sample solution, a capillary pump for sucking it, and a measurement fluidic channel formed between the inlet port and the capillary pump are formed in line in the plane direction of a substrate. In this measurement chip, when a sample solution is introduced from the inlet port, it sequentially flows from the inlet port to the measurement fluidic channel and pump. When the sample solution reaches the capillary pump, it is sucked by the capillary action of the capillary pump. The sample solution which stays at the inlet port flows to the pump through the measurement fluidic channel by the suction force of the capillary pump.

DISCLOSURE OF INVENTION

Problems to be Solved by the Invention

However, in a technique using a conventional capillary pump, components are formed in line in a measurement chip. The position of a fluidic channel used to perform measurement (to be referred to as a measurement fluidic channel) is determined by taking account of other components. In a measurement apparatus, the measurement mechanism is arranged by focusing on a predetermined position of the measurement chip in advance. When performing measurement, the setting of the measurement mechanism of the measurement apparatus needs to be changed in accordance with the position of the measurement fluidic channel, which is cumbersome. Depending on the position of the measurement fluidic channel, the setting of the measurement mechanism needs to be greatly changed, and in some cases, measurement itself is impossible.

When a measurement chip is formed into a predetermined shape, a region assignable to a capillary pump is limited. This limits the capacity of the capillary pump and the time during which a sample solution can flow through the fluidic channel. No sufficient measurement time can sometimes be ensured.

The present invention has been made to solve the above problems, and has as its object to provide a flow cell capable of more reliably measuring a liquid flowing through a fluidic channel.

Means of Solution to the Problems

A flow cell according to the present invention comprises a plate-like member, an inlet port which is formed in the plate-like member and used to supply a liquid, a fluidic channel which is formed in the plate-like member and has one end connected to the inlet port, and a pump which is formed in the plate-like member, connected to the other end of the fluidic channel, and sucks, by a surface tension, the liquid flowing from the inlet port through the fluidic channel, wherein the fluidic channel is formed at almost a center of the plate-like member when viewed from the top, and the pump is formed around the fluidic channel.

Effects of the Invention

According to the present invention, a fluidic channel is formed at almost the center of a plate-like member, so a liquid flowing through the fluidic channel can be measured more reliably. Since a pump is formed around the fluidic channel, the pump capacity can be increased to supply a large amount of liquid for a long time. As a result, the liquid can be measured more reliably.

BEST MODE FOR CARRYING OUT THE INVENTION

[First Embodiment]

The first embodiment according to the present invention will be described in detail with reference to the accompanying drawings.

<Structure of Flow Cell>

Figure 1:
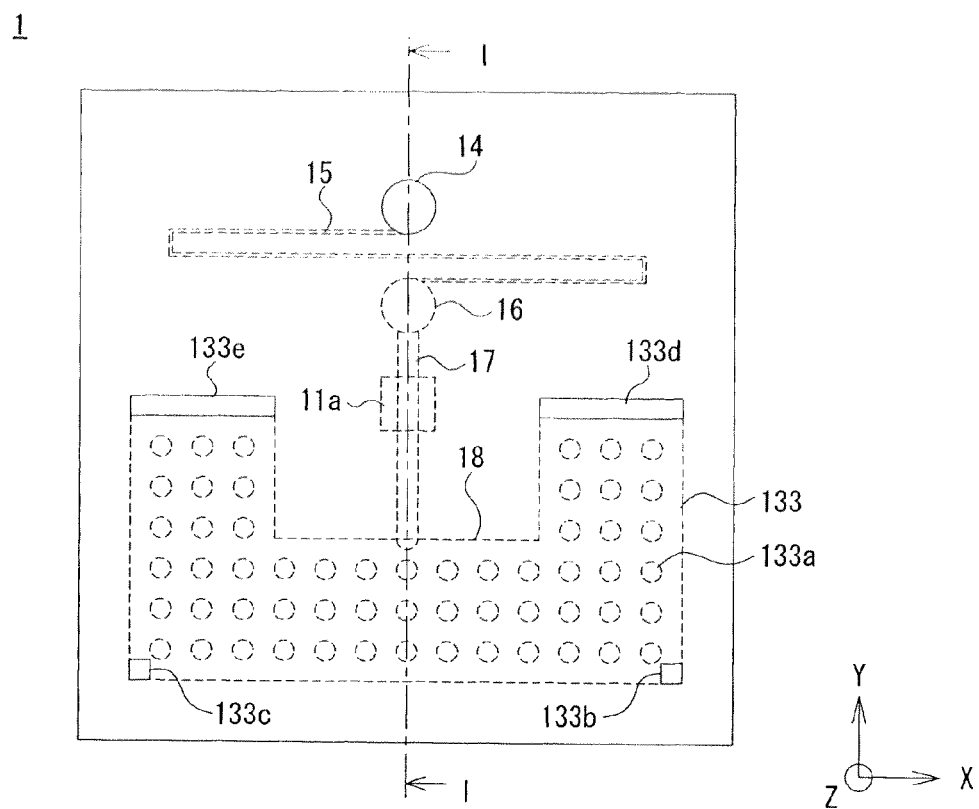
FIG. 1 is a plan view exemplifying the structure of a flow cell in the first embodiment of the present invention.
Figure 2:
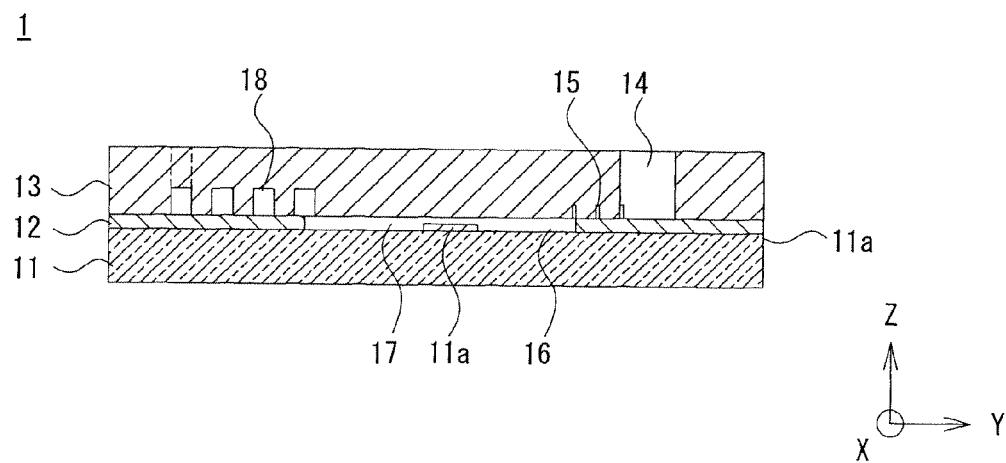
FIG. 2 is a sectional view taken along the line I-I in FIG. 1.
Figure 3:
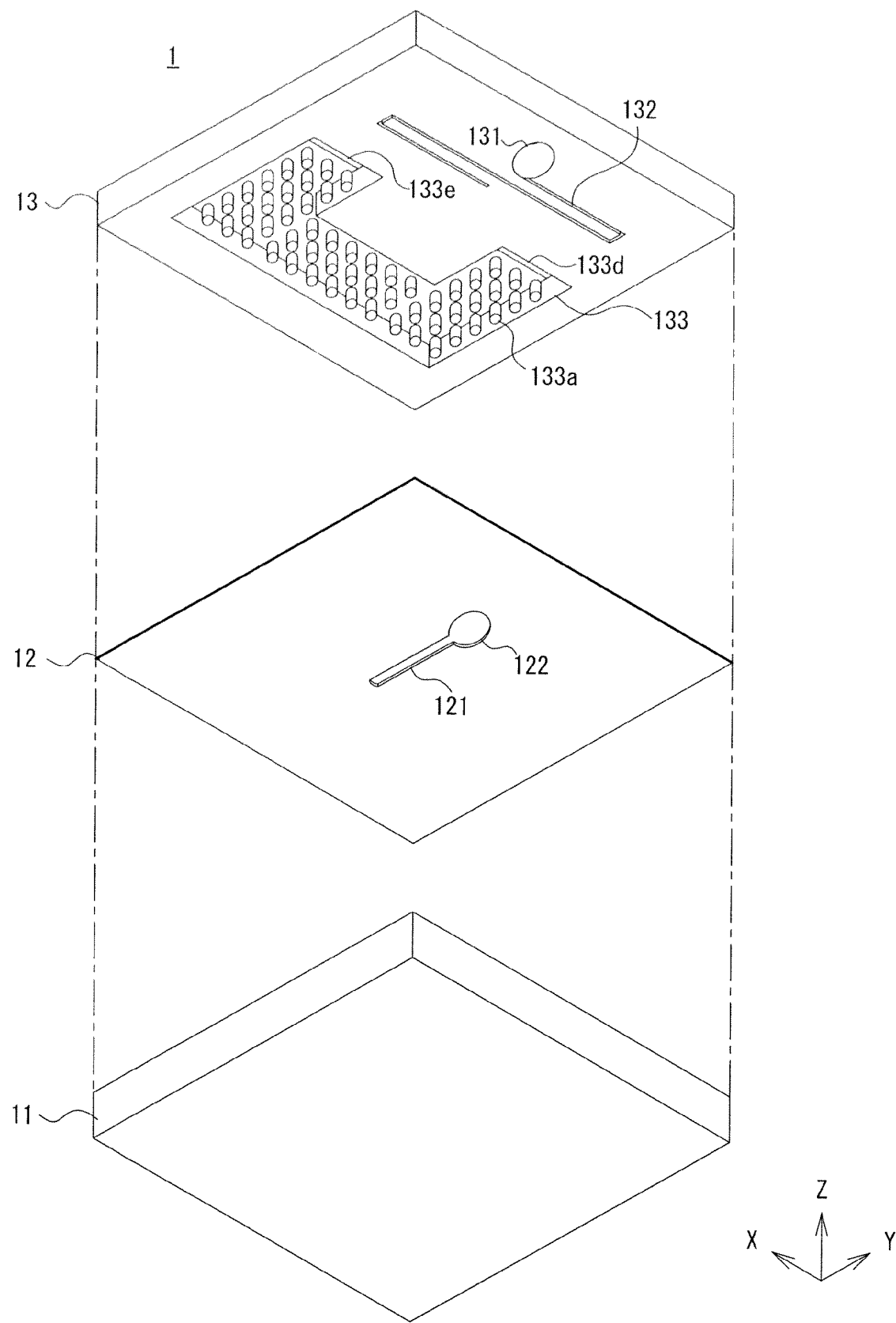
FIG. 3 is an exploded perspective view of the flow cell in FIG. 1 when viewed from the bottom.

As shown in FIGS. 1 to 3, a flow cell 1 according to the first embodiment is formed from a first substrate 11 which has an almost rectangular shape when viewed from the top, a sheet-like member 12 which is disposed on the first substrate 11, and a second substrate 13 which is disposed on the sheet-like member 12. The first substrate 11, sheet-like member 12, and second substrate 13 are stacked to form one plate-like member. The flow cell 1 having this structure includes an inlet port 14 which passes through the second substrate 13 and allows introducing a sample solution, a suction pump 18 which is formed between the sheet-like member 12 and the second substrate 13, and a fluidic channel which connects the suction pump 18 and the inlet port 14. The fluidic channel is made up of a resistance fluidic channel 15 which has one end connected to the inlet port 14 and is formed between the sheet-like member 12 and the second substrate 13, a space 16 which is connected to the other end of the resistance fluidic channel 15 and is formed in the sheet-like member 12 interposed between the first substrate 11 and the second substrate 13, and a measurement fluidic channel 17 which has one end connected to the space 16 and the other end connected to the suction pump 18, is formed in the sheet-like member 12, similar to the space 16, and is irradiated with measurement light or the like by an external device.

<<First Substrate>>

The first substrate 11 is made of optical glass such as BK7, is about 1 mm in thickness, and has an almost rectangular plate-like shape about 16 mm on a side when viewed from the top. An Au layer 11a is selectively formed by plating, vapor deposition, sputtering, or the like on the upper surface of the first substrate 11, i.e., a surface of the first substrate 11 on which the sheet-like member 12 is placed. The material of the first substrate 11 is set in accordance with the properties of light used for measurement, and the like. The Au layer 11a may be formed only at a portion corresponding to the measurement fluidic channel 17 or formed on the entire surface.

<<Sheet-Like Member>>

The sheet-like member 12 is formed from, e.g., a well-known adhesive tape about 10 μm to 150 μm in thickness, and has a planar shape corresponding to the first substrate 11. The sheet-like member 12 has a slit 121 which is formed at almost the center and has an almost rectangular shape when viewed from the top, and an opening 122 which is connected to one end of the slit 121 and has an almost circular shape when viewed from the top. The slit 121 is formed so that its longitudinal direction (Y direction) becomes almost parallel to any one side of the sheet-like member 12.

Together with the upper surface of the first substrate 11 and the lower surface of the second substrate 13, the slit 121 forms the measurement fluidic channel 17 which is an almost rectangular parallelepiped space. A section of the measurement fluidic channel 17 that is perpendicular to the longitudinal direction has dimensions enough to cause capillary action with respect to an aqueous solution.

Together with the upper surface of the first substrate 11 and the lower surface of the second substrate 13, the opening 122 forms the space 16 which is an almost columnar space. The space 16 has sectional dimensions enough to cause capillary action with respect to an aqueous solution.

The sheet-like member 12 can be fabricated by, for example, processing an adhesive tape into a desired shape by a cutter, laser, or the like.

<<Second Substrate>>

The second substrate 13 is formed from, e.g., an acrylic substrate about 0.5 to 5 mm in thickness, and has a planar shape corresponding to the first substrate 11 and sheet-like member 12. A through hole 131 which form he inlet port 14 is formed near the center of the second substrate 13 on its one side. The lower surface of the second substrate 13 has a meandering channel 132 which has one end connected to the through hole 131 and forms the resistance fluidic channel 15, and a cavity 133 which forms the suction pump 18 near the other side opposite to the one side.

The meandering channel 132 has a crank-like planar shape which has a plurality of bent portions, and is repetitively bent in a direction perpendicular to one in which two ends are connected, i.e., the inlet port 14 and space 16 are connected. The bent portion is bent at an almost right angle. The direction (Y direction) in which two ends are connected is almost parallel to the direction of distance between one side and the other side of the second substrate 13.

The cavity 133 is formed from the lower surface toward the upper surface of the second substrate 13. A plurality of almost columnar projections 133a are formed in each cavity and project downward from its ceiling. By setting the projections 133a to have an interval enough to cause capillary action, the cavity 133 functions as the suction pump. The cavity 133 is formed into an almost "U" shape when viewed from the top, so as to surround the center portion of the second substrate 13. In the cavity 133, vents 133b to 133e which pass through the second substrate 13 are formed at two ends near the one side of the second substrate 13 and two corners near the other side.

The through hole 131 forms the inlet port 14 which is an almost columnar space with the upper surface of the sheet-like member 12 defining its bottom.

When the second substrate 13 and sheet-like member 12 are brought into contact with each other, the meandering channel 132 forms the meandering resistance fluidic channel 15. The resistance fluidic channel 15 has sectional dimensions enough to cause capillary action with respect to an aqueous solution.

The internal dimension of the suction pump 18 including the interval, width, and height of the projections 133a in the cavity 133 is set to a value enough to cause capillary action.

The second substrate 13 can be fabricated by injection molding using a mold having a predetermined pattern, laser processing, cutting using an end mill, or the like.

<Method of Manufacturing Flow Cell>

A method of manufacturing the flow cell 1 according to the first embodiment will be exemplified. First, the sheet-like member 12 is placed on the first substrate 11. When the Au layer 11a is formed only at part of the first substrate 11, the sheet-like member 12 is placed on the first substrate 11 so that the slit 121 for forming the measurement fluidic channel 17 is located on the Au layer 11a.

Then, the second substrate 13 is placed on the sheet-like member 12 so that the other end of the meandering channel 132 is positioned in the opening 122 of the sheet-like member 12 and the other end of the slit 121 of the sheet-like member 12 is positioned in the cavity 133.

After the first substrate 11, sheet-like member 12, and second substrate 13 are stacked in this way, they are pressed from the lower surface of the first substrate 11 and the upper surface of the second substrate 13. This fixes the first substrate 11 and second substrate 13 to each other via the sheet-like member 12 formed from a double-faced adhesive tape or the like, completing the flow cell 1 having the inlet port 14, resistance fluidic channel 15, space 16, measurement fluidic channel 17, and suction pump 18.

<Operation of Flow Cell>

The operation of the flow cell 1 according to the first embodiment will be explained.

When a sample solution is injected from the inlet port 14, it proceeds sequentially through the resistance fluidic channel 15, space 16, and measurement fluidic channel 17 by capillary action, and flows into the suction pump 18. In the suction pump 18, a plurality of projections 133a are formed to increase the surface area per unit volume, compared to a structure in which no projection 133a is formed. The inside of the suction pump 18 has dimensions enough to cause capillary action. In the first embodiment, the shape, interval, and the like of the projections 133a are set so that the surface tension which acts on the liquid front of the sample solution in the suction pump 18 becomes larger than that which acts on the liquid front of the sample solution in the inlet port 14.

The sample solution injected from the inlet port 14 passes through the resistance fluidic channel 15, space 16, and measurement fluidic channel 17, flows into the suction pump 18, and proceeds through its inside. Note that the flow rate changes depending on the shape of the cavity 133 such as the outer shape and interval of the projection 133a, the resistance acting on the sample solution, and the like.

In the first embodiment, the measurement fluidic channel 17 is formed at almost the center of the flow cell 1, as shown in FIG. 1. In general, the measurement region of a measurement apparatus is set to focus on almost the center of a measurement chip. When the flow cell 1 according to the first embodiment is mounted in the measurement apparatus, the focus of the measurement region is positioned just above the measurement fluidic channel 17. The measurement apparatus can more reliably measure a sample solution flowing through the measurement fluidic channel 17. This can omit cumbersome resetting of the focus, unlike a conventional flow cell.

In the first embodiment, as shown in FIG. 1, the suction pump 18 having an almost U planar shape to surround the measurement fluidic channel 17 is formed around the measurement fluidic channel 17, i.e., regions except for that on the one-end side (side connected to the space 16) of the measurement fluidic channel 17 when the flow cell 1 is viewed from the top. More specifically, in the flow cell 1 having edges in the X and Y directions, the suction pump 18 is formed in regions between edges of the flow cell 1 in the Y direction and the measurement fluidic channel 17, and a region between the measurement fluidic channel 17 and an edge of the flow cell 1 in the X direction that is positioned on the other-end side of the measurement fluidic channel 17. In this manner, the suction pump 18 is formed in regions around the measurement fluidic channel 17. When the flow cell has the same planar shape as a conventional one, the amount of sample solution which can be supplied can be increased, compared to a conventional structure in which components are formed in line. The time during which a sample solution flows through the fluidic channel can be prolonged, the amount of sample solution can be increased, and the measurement time can also be prolonged. A sample solution flowing through the fluidic channel can be measured more reliably.

[Second Embodiment]

The second embodiment according to the present invention will be described. In the second embodiment, suction pumps are arranged on the two sides of a measurement fluidic channel. In the second embodiment, the same reference numerals as those in the first embodiment denote the same parts, and a description thereof will be properly omitted.

<Structure of Flow Cell>

As shown in FIGS. 4 to 7, a flow cell 2 according to the second embodiment is formed from a first substrate 21 which has an almost rectangular shape when viewed from the top, a sheet-like member 22 which is disposed on the first substrate 21, and a second substrate 23 which is disposed on the sheet-like member 22. The flow cell 2 configured by stacking the substrates and sheet-like member includes an inlet port 24 which passes through the second substrate 23 and allows introducing a sample solution, two suction pumps 27 which are formed between the sheet-like member 22 and the second substrate 23, and a fluidic channel which connects the suction pumps 27 and the inlet port 24. The fluidic channel is made up of a measurement fluidic channel 25 which has one end connected to the inlet port 24 and is formed in the sheet-like member 22 interposed between the first substrate 21 and the second substrate 23, and a resistance fluidic channel 26 which has one end connected to the other end of the measurement fluidic channel 25 and is formed between the sheet-like member 22 and the second substrate 23. In the second embodiment, the resistance fluidic channel 26 is formed between the measurement fluidic channel 25 and the suction pumps 27.

<<First Substrate>>

The first substrate 21 has the same shape and structure as those of the first substrate 11 in the first embodiment. An Au layer 21a is selectively formed on the upper surface of the first substrate 21.

<<Sheet-Like Member>>

The sheet-like member 22 is made of the same material as that of the sheet-like member 12 in the first embodiment, and has the same planar shape. The sheet-like member 22 has a slit 221 which is formed at almost the center and has an almost rectangular shape when viewed from the top, and an opening 222 which is connected to one end of the slit 221 and has an almost circular shape when viewed from the top. The slit 221 is formed so that its longitudinal direction (Y direction) becomes almost parallel to any one side of the sheet-like member 22.

Together with the upper surface of the first substrate 21 and the lower surface of the second substrate 23, the slit 221 forms the measurement fluidic channel 25 which is an almost rectangular parallelepiped space. A section of the measurement fluidic channel 25 that is perpendicular to the longitudinal direction has dimensions enough to cause capillary action with respect to an aqueous solution.

<<Structure of Second Substrate>>

The second substrate 23 has the same shape and structure as those of the second substrate 13 in the first embodiment. A through hole 231 is formed near the center of the second substrate 23 on its one side. The lower surface of the second substrate 23 has a meandering channel 232 which is formed from almost the center to the vicinity of the other side opposite to the one side, and two cavities 233 which are formed on the two sides of the meandering channel 232.

The through hole 231 has the same planar shape as that of the opening 222.

The meandering channel 232 has a crank-like planar shape which has a plurality of bent portions and is bent repetitively in a direction (X direction) perpendicular to the direction (Y direction) of distance between the one side and the other side. The bent portion is smoothly bent into an almost arcuate shape, i.e., curved shape. The other end of the meandering channel 232 branches near the other side of the second substrate 23. The branches extend in opposite directions in the perpendicular direction and are connected to the adjacent cavities 233, respectively.

The cavities 233 are formed from the lower surface toward the upper surface of the second substrate 23. A plurality of almost columnar projections 233a are formed in each cavity and project downward (negative direction in the Z direction) from its ceiling. The cavity 233 is formed into an almost rectangular shape when viewed from the top. Vents 233d and 233e are formed at ends of the cavities 233 near the one side. Vents 233b and 233c are formed at corners of the cavities 233 near the other side that are opposite to corners connected to the branches of the other end of the meandering channel 232. The vents 233b to 233e pass through the second substrate 23.

Together with the opening 222 and the upper surface of the first substrate 21, the through hole 231 forms the inlet port 24 which is an almost columnar space with the upper surface of the first substrate 21 defining its bottom.

When the second substrate 23 and sheet-like member 22 are brought into contact with each other, the meandering channel 232 forms the meandering resistance fluidic channel 26. The resistance fluidic channel 26 has sectional dimensions enough to cause capillary action with respect to an aqueous solution.

The internal dimension of the suction pump 27 including the interval, width, and height of the projections 233a in the cavity 233 is set to a value enough to cause capillary action.

<Method of Manufacturing Flow Cell>

A method of manufacturing the flow cell according to the second embodiment will be exemplified. First, the sheet-like member 22 is placed on the first substrate 21. When the Au layer 21a is formed only at part of the first substrate 21, the sheet-like member 22 is placed on the first substrate 21 so that the slit 221 for forming the measurement fluidic channel 25 is located on the Au layer 21a.

Then, the second substrate 23 is placed on the sheet-like member 22 so that the through hole 231 and opening 222 are connected to each other and one end of the meandering channel 232 is positioned in the other end of the slit 221.

After the first substrate 21, sheet-like member 22, and second substrate 23 are stacked in this fashion, they are pressed from the lower surface of the first substrate 21 and the upper surface of the second substrate 23. This fixes the first substrate 21 and second substrate 23 to each other via the sheet-like member 22 formed from a double-faced adhesive tape or the like, completing the flow cell 2 having the inlet port 24, measurement fluidic channel 25, resistance fluidic channel 26, and suction pumps 27.

<Operation of Flow Cell>

The operation of the flow cell 2 according to the second embodiment will be explained.

Also in the second embodiment, similar to the first embodiment, a plurality of projections 233a are formed in the suction pump 27. A sample solution injected from the inlet port 24 is sucked by the suction pump 27, passes through the measurement fluidic channel 25 and resistance fluidic channel 26, and reaches the suction pump 27.

Figure 4:
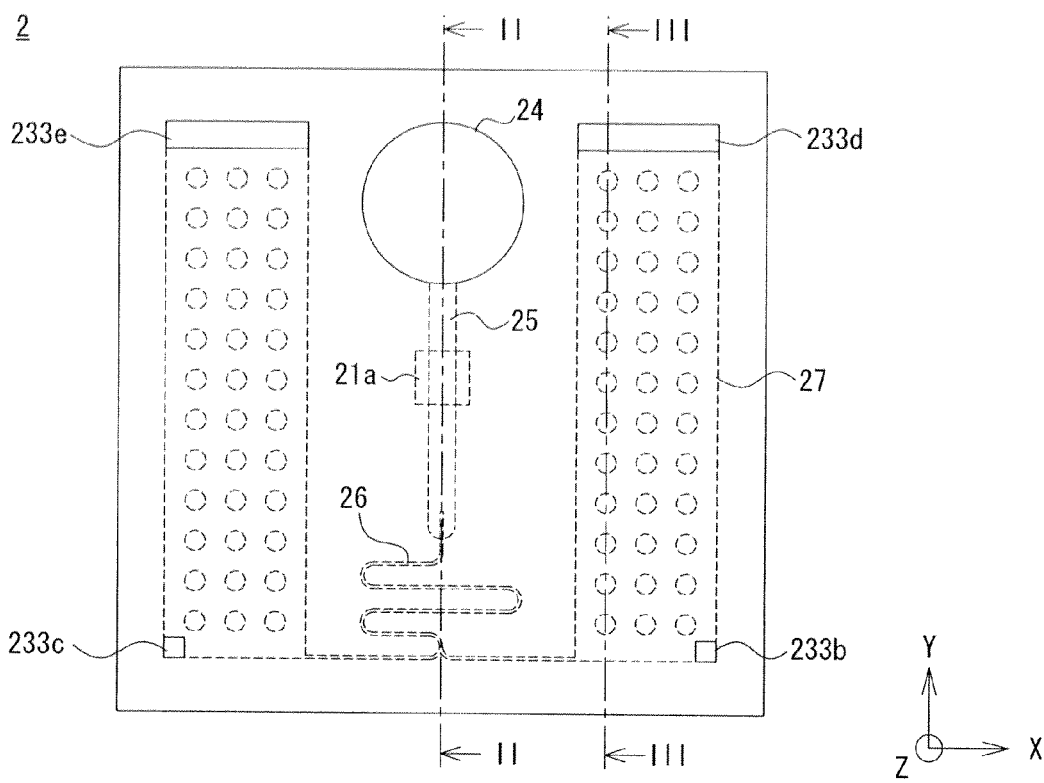
FIG. 4 is a plan view exemplifying the structure of a flow cell in the second embodiment of the present invention.
Figure 5:
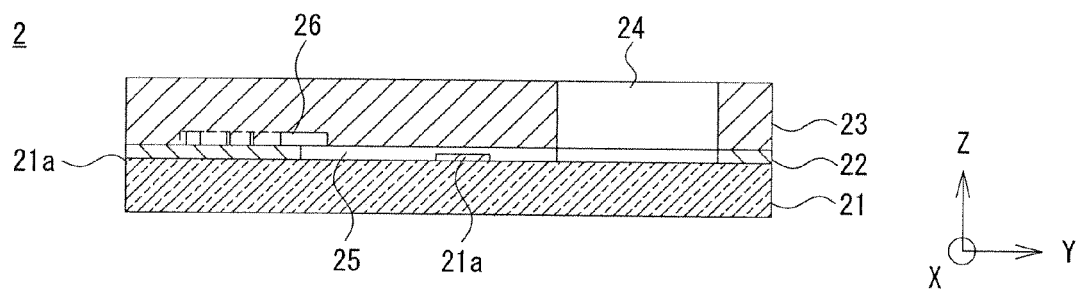
FIG. 5 is a sectional view taken along the line II-II in FIG. 4.
Figure 6:
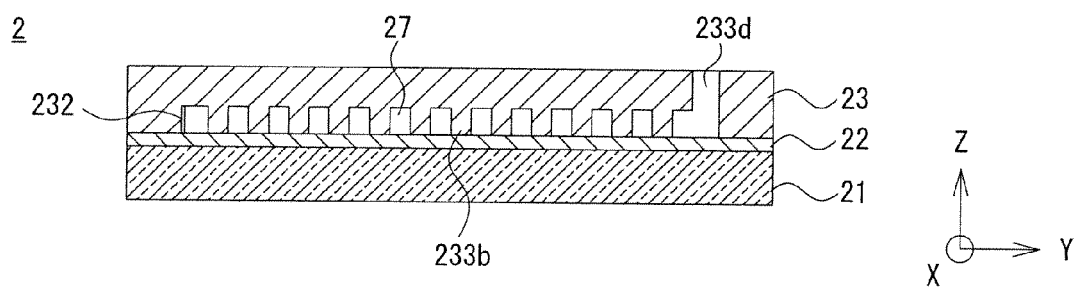
FIG. 6 is a sectional view taken along the line III-III in FIG. 4.
Figure 7:
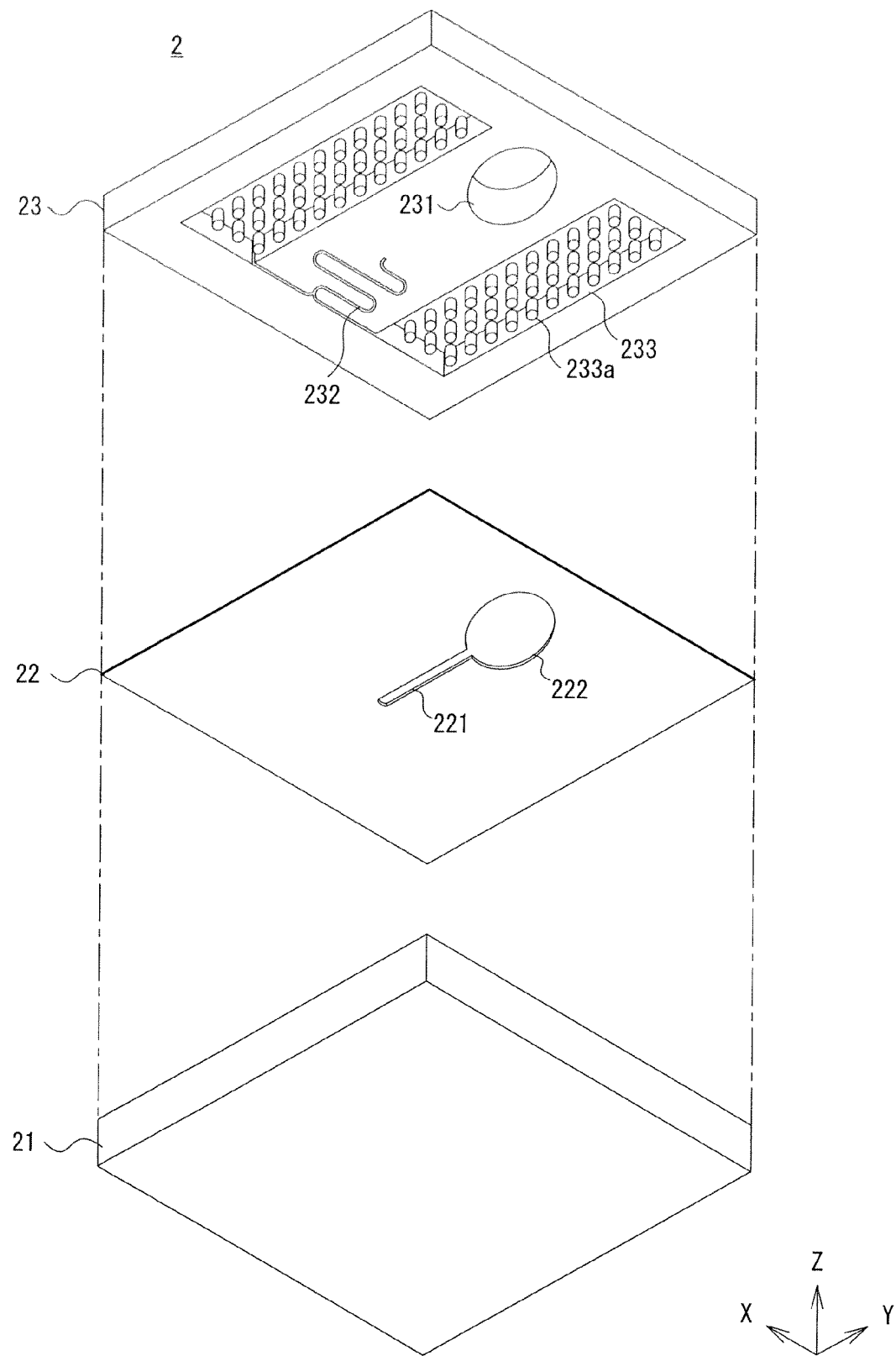
FIG. 7 is an exploded perspective view of the flow cell in FIG. 4 when viewed from the bottom.

Also in the second embodiment, as shown in FIG. 4, the measurement fluidic channel 25 is arranged at almost the center of the flow cell 2. As described above, the measurement region of a measurement apparatus is generally set at almost the center of a measurement chip. When the flow cell 2 according to the second embodiment is mounted in the measurement apparatus, the focus of the measurement region is positioned just above the measurement fluidic channel 25. The measurement apparatus can more reliably measure a sample solution flowing through the measurement fluidic channel 25. This can omit cumbersome resetting of the focus, unlike a conventional flow cell.

In the second embodiment, as shown in FIG. 4, the suction pumps 27 are formed on the two sides of the measurement fluidic channel 25 to extend from the vicinity of one side of the flow cell 2 to that of the other side. In other words, the suction pumps 27 are formed in regions between edges of the flow cell 2 in the Y direction and the measurement fluidic channel 25. In this way, the suction pumps 27 are arranged on the two sides of the measurement fluidic channel 25. When the flow cell has the same planar shape as a conventional one, the amount of sample solution which can be supplied can be increased, compared to a conventional structure in which components are formed in line. The time during which a sample solution flows through the fluidic channel can be prolonged, the amount f sample solution can be increased, and the measurement time can also be prolonged. A sample solution flowing through the fluidic channel can be measured more reliably.

[Third Embodiment]

The third embodiment according to the present invention will be described. The third embodiment is different from the second embodiment in the internal structure of the suction pump. In the third embodiment, the same reference numerals as those in the first and second embodiments denote the same parts, and a description thereof will be properly omitted.

<Structure of Flow Cell>

Figure 8:
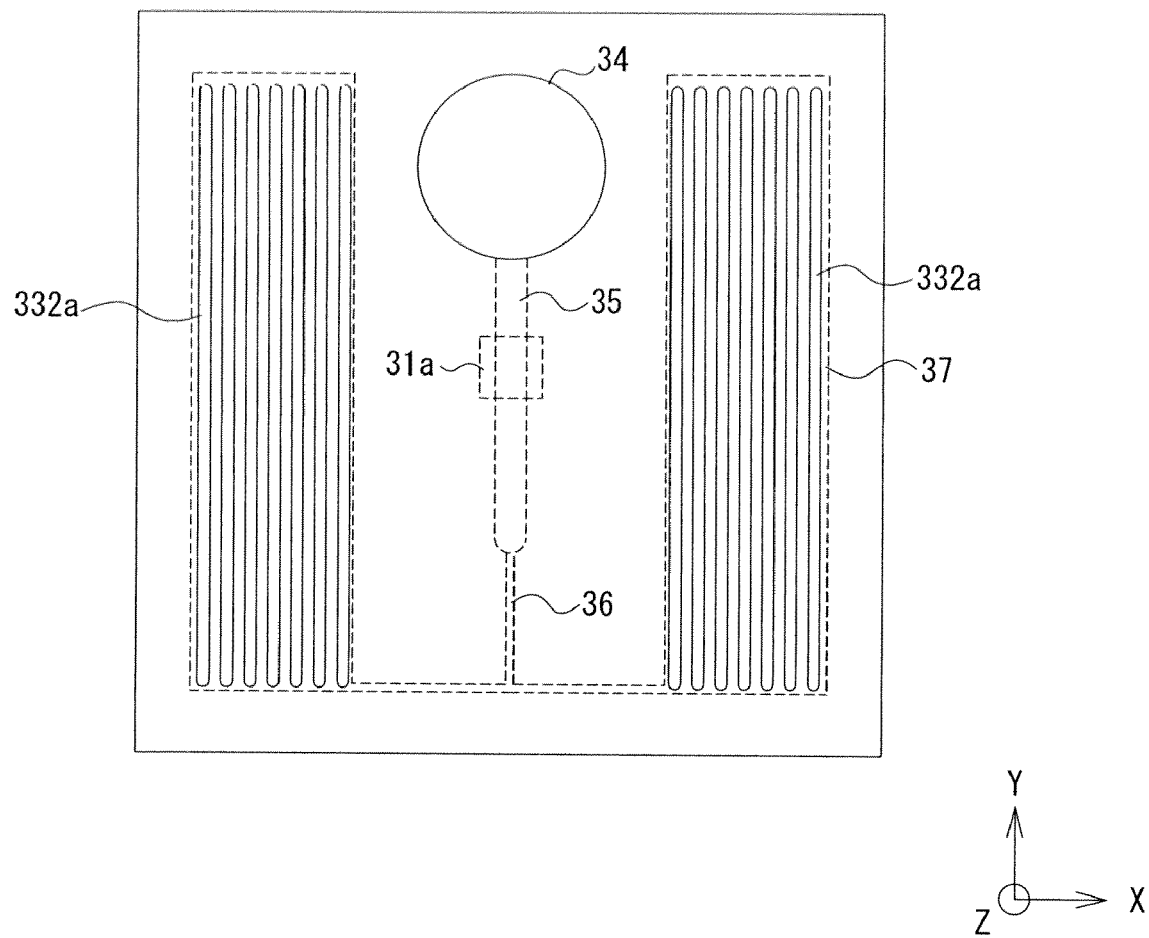
FIG. 8 is a plan view showing the structure of a flow cell in the third embodiment of the present invention.
Figure 9:
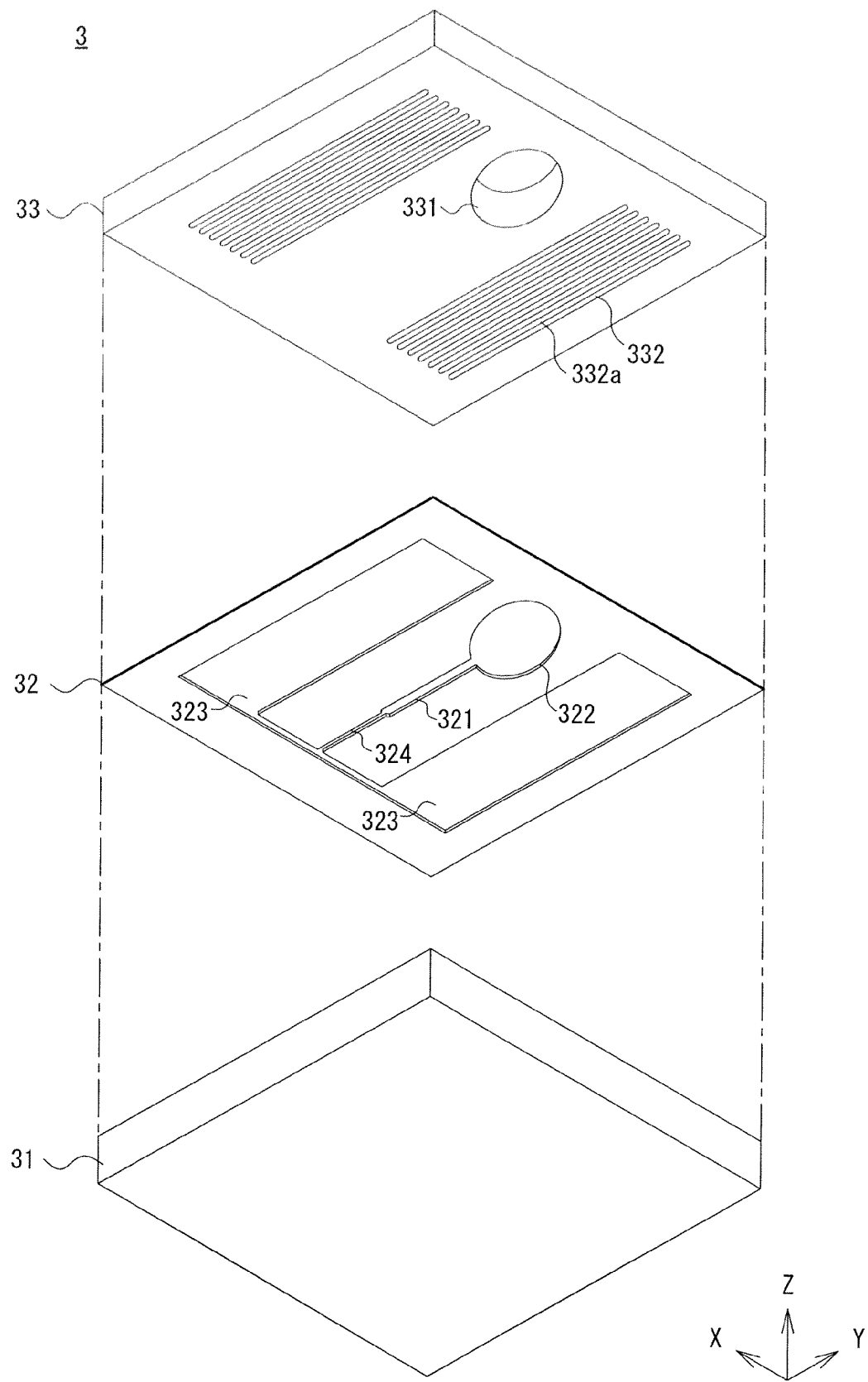
FIG. 9 is an exploded perspective view of the flow cell in FIG. 8 when viewed from the bottom.

As shown in FIGS. 8 and 9, a flow cell 3 according to the third embodiment is formed from a first substrate 31 which has an almost rectangular shape when viewed from the top, a sheet-like member 32 which is disposed on the first substrate 31, and a second substrate 33 which is disposed on the sheet-like member 32. The flow cell 3 configured by stacking the substrates and sheet-like member includes an inlet port 34 which passes through the second substrate 33 and allows introducing a sample solution, two suction pumps 37 which are formed between the sheet-like member 32 and the second substrate 33, and a fluidic channel which connects the suction pumps 37 and the inlet port 34. The fluidic channel is made up of a measurement fluidic channel 35 which has one end connected to the inlet port 34 and is formed in the sheet-like member 32 interposed between the first substrate 31 and the second substrate 33, and a resistance fluidic channel 36 which has one end connected to the other end of the measurement fluidic channel 35 and is formed between the sheet-like member 32 and the second substrate 33.

<<First Substrate>>

The first substrate 31 has the same shape and structure as those of the first substrate 11 in the first embodiment. An Au layer 31a is selectively formed on the upper surface of the first substrate 31.

<<Sheet-like Member>>

The sheet-like member 32 is made of the same material as that of the sheet-like member 12 in the first embodiment, and has the same planar shape. The sheet-like member 32 has a slit 321 which is formed at almost the center and has an almost rectangular shape when viewed from the top, an opening 322 which is connected to one end of the slit 321 and has an almost circular shape when viewed from the top, suction slits 323 which are formed on the two sides of the slit 321 and have an almost rectangular shape when viewed from the top, and a guide slit 324 in which one end is connected to the other end of the slit 321, the other end branches, and the branches are connected to the corresponding suction slits 323. The slit 321 is formed so that its longitudinal direction (Y direction) becomes almost parallel to any one side of the sheet-like member 32.

Together with the upper surface of the first substrate 31 and the lower surface of the second substrate 33, the slit 321 forms the measurement fluidic channel 35 which is an almost rectangular parallelepiped space. A section of the measurement fluidic channel 35 that is perpendicular to the longitudinal direction has dimensions enough to cause capillary action with respect to an aqueous solution.

Together with the upper surface of the first substrate 31 and the lower surface of the second substrate 33, the guide slit 324 forms the resistance fluidic channel 36 which is an almost rectangular parallelepiped space. A section of the resistance fluidic channel 36 that is perpendicular to the longitudinal direction has dimensions enough to cause capillary action with respect to an aqueous solution.

<<Structure of Second Substrate>>

The second substrate 33 has the same shape and structure as those of the second substrate 13 in the first embodiment. A through hole 331 is formed near the center of the second substrate 33 on its one side. The lower surface of the second substrate 33 has two slit portions 332 which are formed on the two sides of almost the center and the through hole 331.

The through hole 331 has the same planar shape as that of the opening 322.

The slit portion 332 extends in a direction (Y direction) in which the one side and the other side of the second substrate 33 are connected. The slit portion 332 includes a plurality of straight slits 332a which pass through the second substrate 33 in the direction of thickness. The slits 332a are spaced apart from adjacent ones at predetermined intervals. The slit portion 332 has almost the same outer shape as that of the corresponding suction slit 323.

Together with the opening 322 and the upper surface of the first substrate 31, the through hole 331 forms the inlet port 34 which is an almost columnar space with the upper surface of the first substrate 31 defining its bottom.

Together with the upper surface of the first substrate 31 and the suction slit 323, the slit portion 332 forms the suction pump 37. The internal dimension of the suction pump 37 including the interval and width of the slits 332a in the slit portion 332 is set to a value enough to cause capillary action.

<Method of Manufacturing Flow Cell>

A method of manufacturing the flow cell 3 according to the third embodiment will be exemplified. First, the sheet-like member 32 is placed on the first substrate 31. When the Au layer 31a is formed only at part of the first substrate 31, the sheet-like member 32 is placed on the first substrate 31 so that the slit 321 for forming the measurement fluidic channel 35 is located on the Au layer 31a.

Then, the second substrate 33 is placed on the sheet-like member 32 so that the through hole 331 and opening 322 are connected to each other and the slit portions 332 are positioned in the suction slits 323.

After the first substrate 31, sheet-like member 32, and second substrate 33 are stacked in this manner, they are pressed from the lower surface of the first substrate 31 and the upper surface of the second substrate 33. This fixes the first substrate 31 and second substrate 33 to each other via the sheet-like member 32 formed from a double-faced adhesive tape or the like, completing the flow cell 3 having the inlet port 34, measurement fluidic channel 35, resistance fluidic channel 36, and suction pumps 37.

<Operation of Flow Cell>

The operation of the flow cell 3 according to the third embodiment will be explained.

When a sample solution is injected from the inlet port 34, it proceeds sequentially through the measurement fluidic channel 35 and resistance fluidic channel 36 by capillary action, and flows into the suction pumps 37. In the suction pumps 37, a plurality of slits 332a are formed to increase the surface area per unit volume, compared to a structure in which no slit 332a is formed. The inside of the suction pump 37 has dimensions enough to cause capillary action. In the third embodiment, the shape, interval, and the like of the slits 332a are set so that the surface tension which acts on the liquid front of the sample solution in the suction pump 37 becomes larger than that which acts on the liquid front of the sample solution in the inlet port 34.

The sample solution injected from the inlet port 34 passes through the measurement fluidic channel 35 and resistance fluidic channel 36, flows into the suction pumps 37, and proceeds through the slits 332a, which form the suction pumps 37, in the direction in which the slits 332a extend and the direction of height. Note that the flow rate changes depending on the shape of the slit portion 332 such as the outer shape and interval of the slit 332a, the resistance acting on the sample solution, and the like.

Also in the third embodiment, the measurement fluidic channel 35 is formed at almost the center of the flow cell 3, as shown in FIG. 8. When the flow cell 3 according to the third embodiment is mounted in the measurement apparatus, the focus of the measurement region is positioned just above the measurement fluidic channel 35. The measurement apparatus can more reliably measure a sample solution flowing through the measurement fluidic channel 35. This can omit cumbersome resetting of the focus, unlike a conventional flow cell.

Also in the third embodiment, as shown in FIG. 8, the suction pumps 27 are formed on the two sides of the measurement fluidic channel 35 to extend from the vicinity of one side of the flow cell 3 to that of the other side. In other words, the suction pumps 37 are formed in regions between edges of the flow cell 3 in the Y direction and the measurement fluidic channel 35. In this manner, the suction pumps 37 are arranged on the two sides of the measurement fluidic channel 35. When the flow cell has the same planar shape as a conventional one, the amount of sample solution which can be supplied can be increased, compared to a conventional structure in which components are formed in line. The time during which a sample solution flows through the fluidic channel can be prolonged, the amount of sample solution can be increased, and the measurement time can also be prolonged. A sample solution flowing through the fluidic channel can be measured more reliably.

[Fourth Embodiment]

The fourth embodiment according to the present invention will be described. The fourth embodiment is different from the first to third embodiments in the structure of the suction pump. In the fourth embodiment, the same reference numerals as those in the first to third embodiments denote the same parts, and a description thereof will be properly omitted.

<Structure of Flow Cell>

Figure 10:
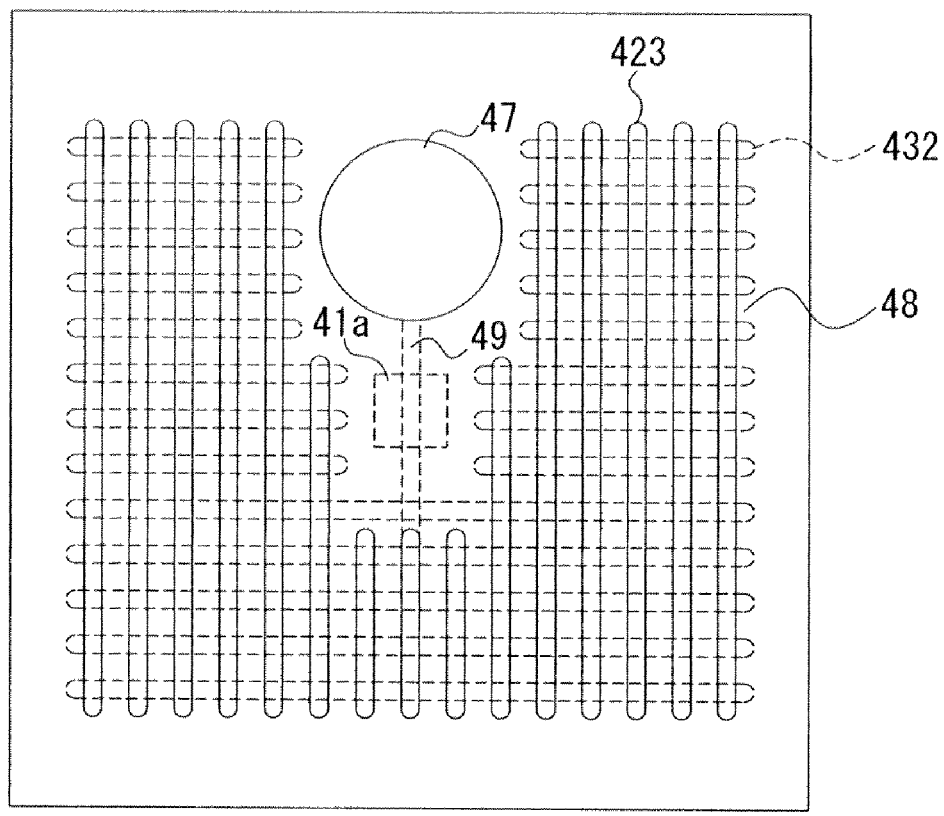
FIG. 10 is a plan view showing the structure of a flow cell in the fourth embodiment of the present invention.
Figure 11:
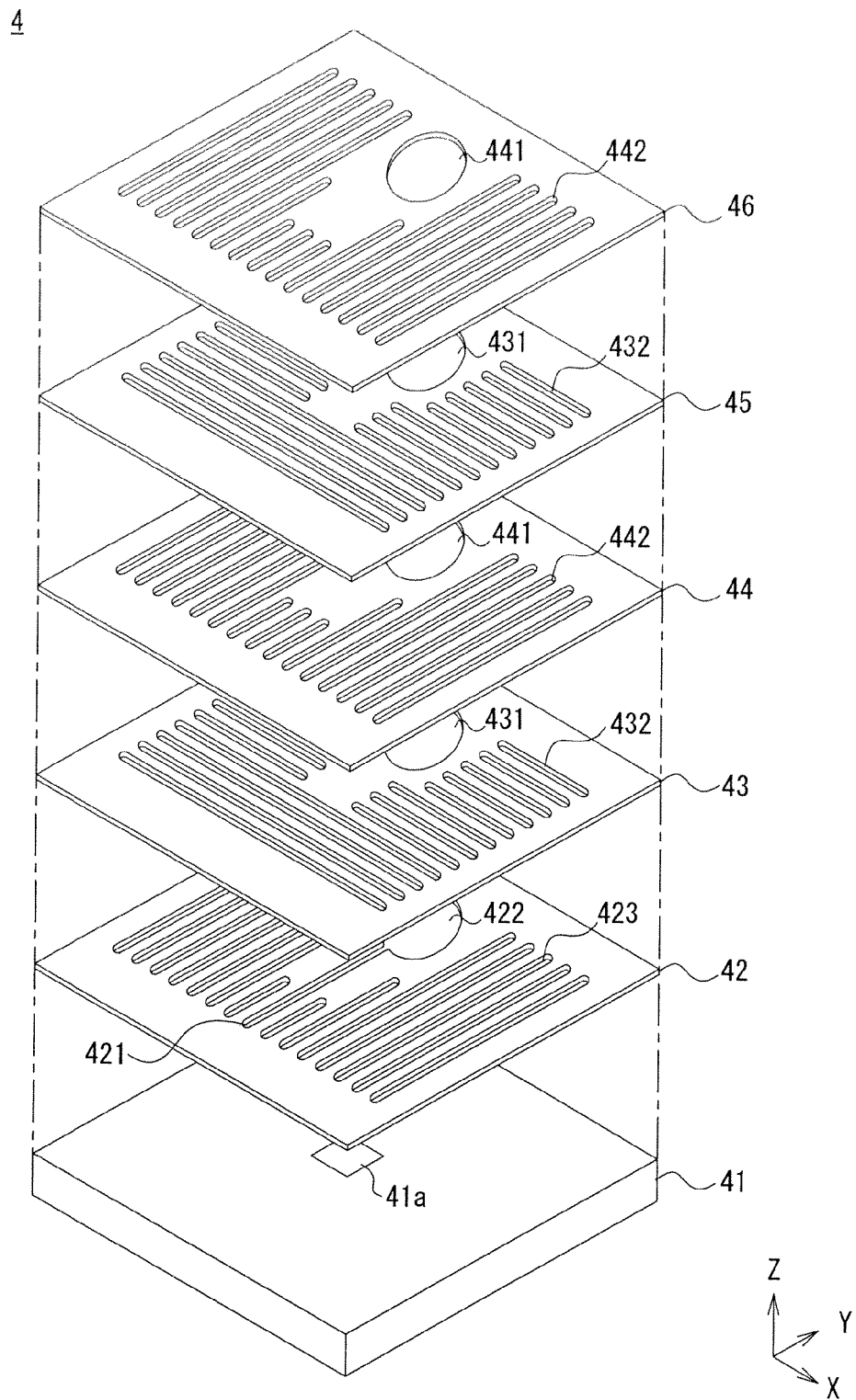
FIG. 11 is an exploded perspective view of the flow cell in FIG. 10 when viewed from the top.

As shown in FIGS. 10 and 11, a flow cell 4 according to the fourth embodiment is formed from a first substrate 41 which has an almost rectangular shape when viewed from the top, a first sheet-like member 42 which is disposed on the first substrate 41, a second sheet-like member 43 which is disposed on the first sheet-like member 42, a third sheet-like member 44 which is disposed on the second sheet-like member 43, a fourth sheet-like member 45 which is disposed on the third sheet-like member 44, and a fifth sheet-like member 46 which is disposed on the fourth sheet-like member 45. The flow cell 4 configured by stacking the substrate and sheet-like members includes an inlet port 47 which passes through the first to fifth sheet-like members 42 to 46 and allows introducing a sample solution, a suction pump 48 which is formed from the first to fifth sheet-like members 42 to 46, has an almost U shape when viewed from the top, and incorporates a plurality of fluidic channels disposed in a checkerboard pattern, and a measurement fluidic channel 49 which has one end connected to the inlet port 47 and the other end connected to the pump 48.

In the fourth embodiment, the second sheet-like member 43 and fourth sheet-like member 45 have the same structure, while the third sheet-like member 44 and fifth sheet-like member 46 have the same structure. Thus, a description of these sheet-like members will be properly omitted.

<<First Substrate>>

The first substrate 41 has the same shape and structure as those of the first substrate 11 in the first embodiment. An Au layer 41a is selectively formed on the upper surface of the first substrate 41.

<<First Sheet-Like Member>>

The first sheet-like member 42 is made of the same material as that of the sheet-like member 12 in the first embodiment, and has the same planar shape. The first sheet-like member 42 has a measurement slit 421 which is formed at almost the center and has an almost rectangular shape when viewed from the top, an opening 422 which is connected to one end of the measurement slit 421 and has an almost circular shape when viewed from the top, and a plurality of Y slits 423 which are formed around the measurement slit 421 and opening 422 The Y slits 423 extend in the same direction (Y direction) as that of the measurement slit 421, and are spaced apart from adjacent ones at predetermined intervals. The Y slits 423 are formed at positions except for those corresponding to the Au layer 41a and its vicinity when the flow cell 4 is viewed from a direction in which the first substrate 41 and the first to fifth sheet-like members 42 to 46 are stacked.

Together with the upper surface of the first substrate 41 and the lower surface of the second sheet-like member 43, the measurement slit 421 forms the measurement fluidic channel 49 which is an almost rectangular parallelepiped space. A section of the measurement fluidic channel 49 that is perpendicular to the longitudinal direction has dimensions enough to cause capillary action with respect to an aqueous solution.

Together with the upper surface of the first substrate 41 and the lower surface of the second sheet-like member 43, the Y slits 423 form fluidic channels in the Y direction that form part of the suction pump 48. These fluidic channels are connected to those formed by X slits 432 (to be described later) of the second sheet-like member 43 at positions where the fluidic channels overlap each other in the stacking direction. The dimension of the fluidic channel is set to a value enough to cause capillary action.

The shapes of the measurement slit 421 and the like formed in the first sheet-like member 42 and the second to fifth sheet-like members 43 to 46 can be formed using a laser beam machine, cutting plotter, or the like.

<<Second and Fourth Sheet-Like Members>>

The second and fourth sheet-like members 43 and 45 are made of the same material as that of the sheet-like member 12 in the first embodiment, and have the same planar shape. Each of the second and fourth sheet-like members 43 and 45 has an opening 431 which is formed at the same position as that of the opening 422 of the first sheet-like member 42, and a plurality of X slits 432 which are formed at positions except for the position of the opening 431 and almost the center of the second or fourth sheet-like member 43 or 45. The X slits 432 extend in a direction (X direction) perpendicular to the measurement slit 421, and are spaced apart from adjacent ones at predetermined intervals. The X slits 432 are formed at positions except for those corresponding to the Au layer 41a and its vicinity when the flow cell 4 is viewed from a direction in which the first substrate 41 and the first to fifth sheet-like members 42 to 46 are stacked.

Together with the upper surface of the first sheet-like member 42 and the lower surface of the third sheet-like member 44, or the upper surface of the third sheet-like member 44 and the lower surface of the fifth sheet-like member 46, the X slits 432 form fluidic channels in the X direction that form part of the suction pump 48. These fluidic channels are connected to those formed by the Y slits 423 of the first sheet-like member 42, or those formed by Y slits 442 (to be described later) of the third or fifth sheet-like member 44 or 46 at positions where the fluidic channels overlap each other in the stacking direction. The dimension of the fluidic channel is set to a value enough to cause capillary action.

<<Third and Fifth Sheet-Like Members>>

The third and fifth sheet-like members 44 and 46 are made of the same material as that of the sheet-like member 12 in the first embodiment, and have the same planar shape. Each of the third and fifth sheet-like members 44 and 46 has an opening 441 which is formed at the same position as that of the opening 422 of the first sheet-like member 42, and a plurality of Y slits 442 which are formed at positions except for the position of the opening 441 and almost the center of the third or fifth sheet-like member 44 or 46. The Y slits 442 extend in the same direction (Y direction) as that of the measurement slit 421, and are spaced apart from adjacent ones at predetermined intervals. The Y slits 442 are formed at positions except for those corresponding to the Au layer 41a and its vicinity when the flow cell 4 is viewed from a direction in which the first substrate 41 and the first to fifth sheet-like members 42 to 46 are stacked.

Together with the upper surface of the second sheet-like member 43 and the lower surface of the fourth sheet-like member 45, or the upper surface of the fourth sheet-like member 45, the Y slits 442 form fluidic channels in the Y direction that form part of the suction pump 48. These fluidic channels are connected to those formed by the X slits 432 of the second or fourth sheet-like member 43 or 45 at positions where the fluidic channels overlap each other in the stacking direction. The dimension of the fluidic channel is set to a value enough to cause capillary action.

<Method of Manufacturing Flow Cell>

A method of manufacturing the flow cell 4 according to the fourth embodiment will be exemplified. First, the first sheet-like member 42 is placed on the first substrate 41. When the Au layer 41a is formed only at part of the first substrate 41, the first sheet-like member 42 is placed on the first substrate 41 so that the measurement slit 421 for forming the measurement fluidic channel 49 is located on the Au layer 41a.

Then, the second to fifth sheet-like members 43 to 46 are sequentially stacked on the first sheet-like member 42 so that the openings 431 and 441 are connected to each other. The first substrate 41 and the first to fifth sheet-like members 42 to 46 are pressed from the lower surface of the first substrate 41 and the upper surface of the fifth sheet-like member 46. The first to fifth sheet-like members 42 to 46 each formed from a double-faced adhesive tape or the like, and the first substrate 41 are fixed to each other, completing the flow cell 4 having the inlet port 47, suction pump 48, and measurement fluidic channel 49.

<Operation of Flow Cell>

The operation of the flow cell 4 according to the fourth embodiment will be explained.

When a sample solution is injected from the inlet port 47, it proceeds through the measurement fluidic channel 49 by capillary action, passes above the Au layer 41a, and proceeds to the other end of the measurement fluidic channel 49. Fluidic channels formed by the X slits 432 that form the suction pump 48 are connected above the other end. In the suction pump 48 including the fluidic channels, a plurality of fluidic channels are disposed in a checkerboard pattern to increase the surface area per unit volume, compared to a suction pump having no such structure. The inside of the suction pump 48 thus has dimensions enough to cause capillary action. In the fourth embodiment, the shape, interval, and the like of the fluidic channels in the suction pump 48 are set so that the surface tension which acts on the liquid front of the sample solution in the suction pump 48 becomes larger than that which acts on the liquid front of the sample solution in the inlet port 47.

The sample solution injected from the inlet port 47 passes through the measurement fluidic channel 49, flows into the suction pump 48, and proceeds through the fluidic channels, which form the suction pump 48 and are disposed in a checkerboard pattern, in the direction in which the fluidic channels extend and the direction of height. Note that the flow rate changes depending on the shapes of the Y slits 423 and 442, the thicknesses of the first to fifth sheet-like members 42 to 46, the resistance acting on the sample solution, and the like.

Also in the fourth embodiment, the measurement fluidic channel 49 is formed at almost the center of the flow cell 4, as shown in FIG. 10. When the flow cell 4 according to the fourth embodiment is mounted in the measurement apparatus, the focus of the measurement region is positioned just above the measurement fluidic channel 49. The measurement apparatus can more reliably measure a sample solution flowing through the measurement fluidic channel 49. This can omit cumbersome resetting of the focus, unlike a conventional flow cell.

Also in the fourth embodiment, as shown in FIG. 10, the suction pump 48 having an almost U planar shape is formed around the measurement fluidic channel 49, i.e., regions except for that on the one-end side (side connected to the inlet port 47) of the measurement fluidic channel 49 when the flow cell 4 is viewed from the top. More specifically, in the flow cell 4 having edges in the X and Y directions, the suction pump 48 is formed in regions between edges of the flow cell 4 in the Y direction and the measurement fluidic channel 49, and a region between the measurement fluidic channel 49 and an edge of the flow cell 4 in the X direction that is positioned on the other-end side of the measurement fluidic channel 49. In this fashion, the suction pump 48 is formed in regions around the measurement fluidic channel 49. When the flow cell has the same planar shape as a conventional one, the amount of sample solution which can be supplied can be increased, compared to a conventional structure in which components are formed in line. The time during which a sample solution flows through the fluidic channel can be prolonged, the amount of sample solution can be increased, and the measurement time can also be prolonged. A sample solution flowing through the fluidic channel can be measured more reliably.

[Fifth Embodiment]

The fifth embodiment according to the present invention will be described.

<Structure of Flow Cell>

Figure 12:
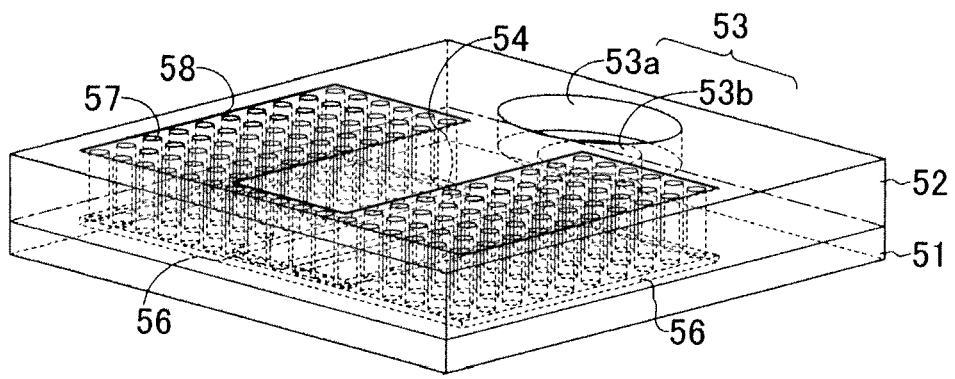
FIG. 12 is a perspective view showing the structure of a flow cell in the fifth embodiment of the present invention.
Figure 13:
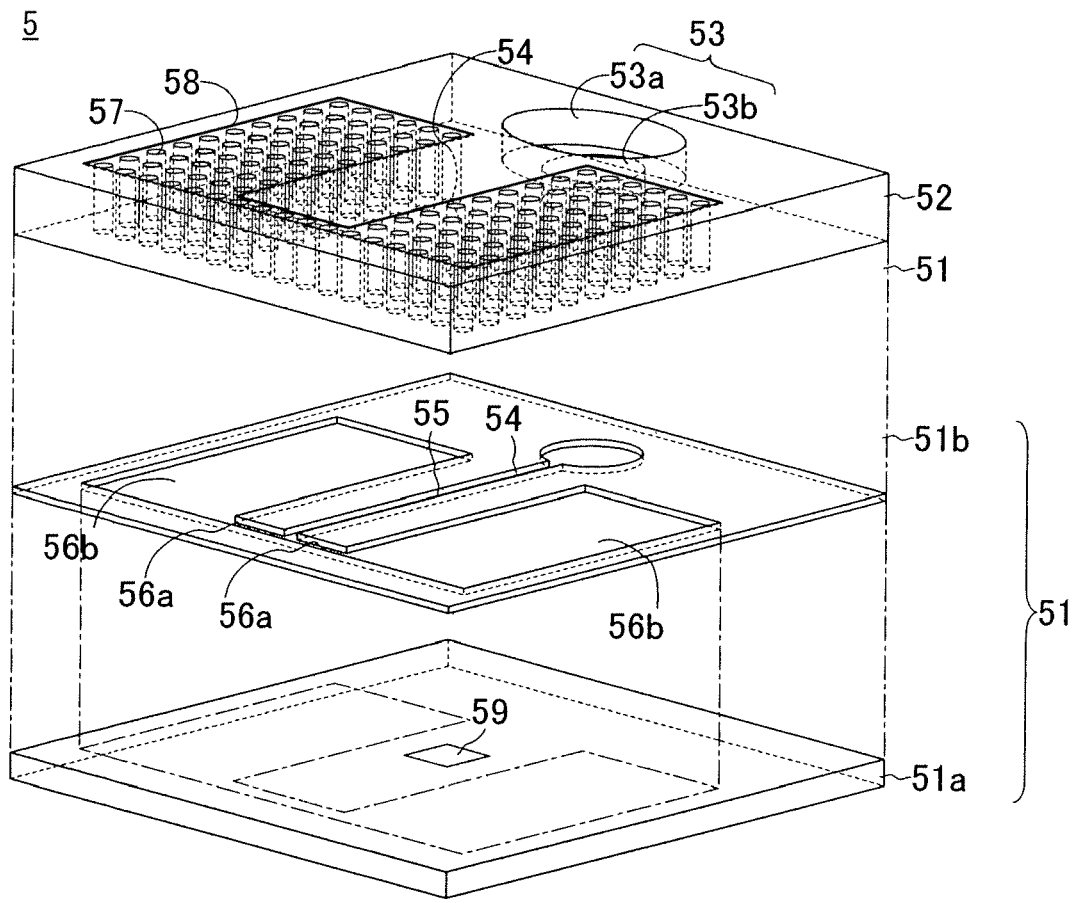
FIG. 13 is a perspective view showing the structure of the flow cell in the fifth embodiment of the present invention.
Figure 14:
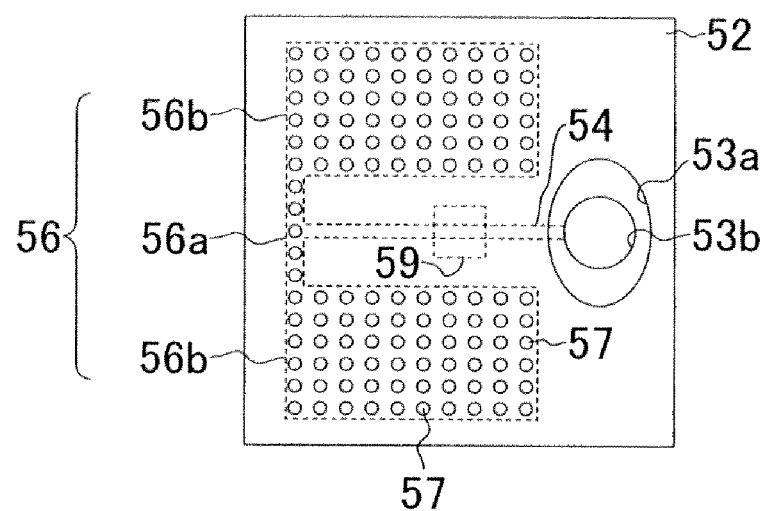
FIG. 14 is a plan view showing the structure of the flow cell in the fifth embodiment of the present invention.

As shown in FIGS. 12 to 14, a flow cell 5 according to the fifth embodiment includes a lower substrate (first substrate) 51 made of a material such as glass in which light is transmissive, an upper substrate (second substrate) 52 which is arranged on the lower substrate 51, an inlet port 53 which is formed in the upper substrate 52 and allows introducing a sample solution, and a fluidic channel 54 which is arranged between opposite surfaces of the lower substrate 51 and upper substrate 52, has one end connected to the inlet port 53, and transfers a sample solution. The fluidic channel 54 is arranged to cross the center of the flow cell 5. The upper substrate 52 is formed to have a plate thickness of about 3 mm, and the lower substrate 51 is formed to have a plate thickness of about 1 mm. The fluidic channel 54 is formed to have a width of 1 mm and a height of about 10 to 100 μm.

The flow cell 5 in the fifth embodiment includes a detecting portion 55 which is arranged at an intermediate portion of the fluidic channel 54, a suction fluidic channel 56 which is arranged between opposite surfaces of the lower substrate 51 and upper substrate 52 and is connected to the other end of the fluidic channel 54, and a plurality of through holes 57 which pass through the upper substrate 52 to reach the suction fluidic channel 56. The through hole 57 has, e.g., a cylindrical shape (cylindrical pipe). A recess is formed in the outer surface of the upper substrate 52 in correspondence with a region (region of the suction fluidic channel 56) where the through holes 57 are formed, thereby forming a discharge portion 58. At the detecting portion 55 of the fluidic channel 54, an Au metal thin film 59 is formed on a surface of the lower substrate 51 that is exposed to the fluidic channel.

The fluidic channel 54 has sectional dimensions enough to cause capillary action with respect to a liquid. Similarly, the through hole 57 has a diameter enough to cause capillary action with respect to a liquid. The distance between the lower substrate 51 and the upper substrate 52 of the suction fluidic channel 56 in a direction (vertical direction) in which they 51 and 52 face each other is set so that, when a liquid enters the fluidic channel 54, it can simultaneously contact the upper and lower surfaces of the suction fluidic channel 56. In other words, the distance is set not to form a gap in the vertical direction of the suction fluidic channel when a liquid enters the suction fluidic channel 56.

In the flow cell 5 of the fifth embodiment, for example, the lower substrate 51 is made up of a base substrate 51a and spacer 51b, as shown in FIG. 13. An opening formed to hollow the spacer 51b forms the fluidic channel 54 and suction fluidic channel 56. The metal thin film 59 is formed on the base substrate 51a in correspondence with a prospective region to serve as the detecting portion 55. In this case, the base substrate 51a is made of glass, and the spacer 51b is made of a resin film.

In the fifth embodiment, as shown in FIG. 14, the suction fluidic channel 56 is expanded and arranged on the two sides of the fluidic channel 54 of the flow cell 5. On each side of the fluidic channel 54, the suction fluidic channel 56 has a coupling portion 56a which is coupled to the fluidic channel 54, and a main suction portion 56b. At the coupling portion 56a, one through hole 57 is arranged in the widthwise direction of the coupling portion 56a. At the main suction portion 56b, a plurality of through holes 57 are two-dimensionally arrayed in the plane direction of the lower substrate 51 (upper substrate 52). At the coupling portion 56a, two or more through holes 57 may be arranged in the widthwise direction. The suction fluidic channel 56 is formed to be wider than the fluidic channel 54 in dimension (width) in a direction perpendicular to the vertical direction of the lower substrate 51 and upper substrate 52 and a direction in which a liquid flows through the fluidic channel 54 (direction in which the fluidic channel 54 extends). A plurality of lines of through holes 57 are arranged in the widthwise direction, and are arrayed in the fluidic channel direction perpendicular to the widthwise direction.

<Operation of Flow Cell>

In the flow cell 5 of the fifth embodiment, a sample solution introduced from the inlet port 53 flows through the fluidic channel 54 by capillary action, and enters the suction fluidic channel 56. The sample solution which has reached the suction fluidic channel 56 is sucked by the through holes 57 by a capillary action. The sample solution which has been introduced from the inlet port 53 and sucked by the through holes 57 in the suction fluidic channel 56 flows through the fluidic channel 54 at a predetermined flow rate in the direction of the suction fluidic channel 56.

In the flow cell 5 according to the fifth embodiment, the suction fluidic channel 56 having a plurality of through holes 57 functions as a suction pump for supplying a sample solution introduced from the inlet port 53 to the fluidic channel 54 at a predetermined flow rate.

Also in the fifth embodiment, the fluidic channel 54 is arranged at almost the center of the flow cell 5, as shown in FIG. 14. When the flow cell 5 according to the fifth embodiment is mounted in the measurement apparatus, the focus of the measurement region is positioned just above the fluidic channel 54. The measurement apparatus can more reliably measure a sample solution flowing through the fluidic channel 54. This can omit cumbersome resetting of the focus, unlike a conventional flow cell.

In the flow cell 5 according to the fifth embodiment, as shown in FIG. 14, the suction fluidic channel 56 (main suction portion 56b) is expanded and arranged on the sides (two sides) of the fluidic channel 54. The region of the suction fluidic channel 56 can be enlarged without greatly increasing the area of the whole flow cell 5. When the flow cell has the same planar shape as a conventional one, the amount of sample solution which can be supplied can be increased, compared to a conventional structure in which components are formed in line. The time during which a sample solution flows through the fluidic channel can be prolonged, the amount of sample solution can be increased, and the measurement time can also be prolonged. A sample solution flowing through the fluidic channel can be measured more reliably.

[Application Example of Flow Cell]

An application example of the flow cell exemplified in each of the first to fifth embodiments will be described briefly. The flow cell is applied to measurement using a well-known surface plasmon resonance phenomenon (Japanese Patent Laid-Open No. 2001-194298 and Japanese Patent Laid-Open No. 2002-214131). Measurement using the surface plasmon resonance phenomenon utilizes resonance of an evanescent wave and surface plasmon wave on a metal surface in contact with an analyte to be measured.

Figure 15:
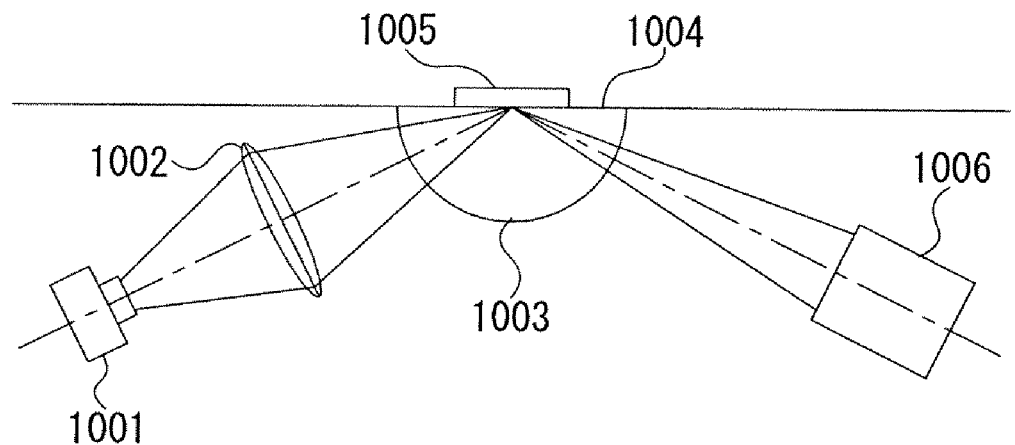
FIG. 15 is a view exemplifying the arrangement of an SPR measurement apparatus.

In this measurement, as shown in FIG. 15, light emitted by a light source 1001 is focused by an entrance lens 1002 and enters a prism 1003. The light irradiates an Au film functioning as the measuring portion of a flow cell 1005 in tight contact with an upper surface 1004 of the prism 1003. The Au thin film is formed in the flow cell 1005, and an analyte is set in contact with the surface of the Au thin film. The focused light which passed through the flow cell 1005 irradiates the lower surface of the Au thin film. The irradiated and focused light is reflected by the lower surface of the Au thin film. A photodetector 1006 formed from an image sensing element such as a CCD image sensor measures the intensity (light intensity). Then, a dip exhibiting a decrease in reflectance is observed at an angle at which the resonance occurs.

This measurement detects the presence/absence of an analyte which selectively binds to an antibody or DNA fragment immobilized on the surface (on the side of a detecting portion) of the Au film. In a state in which a sample solution is set at the detecting portion, a change caused by a reaction between the target analyte and the antibody and a change caused by a foreign substance settled and deposited at the detecting portion cannot be discriminated. Considering this, the sample solution is kept flowing at the detecting portion, suppressing sedimentation of a foreign substance. The change caused by a reaction can be selectively detected.

In the flow cells according to the first to fifth embodiments, a sheet-like member is arranged, but the flow cell may be formed from the first and second substrates without arranging the sheet-like member. In this case, the slit formed in the sheet-like member is formed in the first or second substrate. A member to engage with the sides of the first and second substrates is attached to join them. Alternatively, the first and second substrates are bonded to each other using an adhesive or the like.

In the first to fifth embodiments, the whole flow cell has an almost rectangular shape when viewed from the top. However, the planar shape of the flow cell is not limited to this and can be freely set in accordance with the shape of, e.g., a measurement apparatus in which the flow cell is mounted.

In the first embodiment, the bent portion of the meandering channel 132 which forms the resistance fluidic channel 15 is bent at an almost right angle, but may be smoothly bent into an almost arcuate shape, i.e., curved shape, similar to the second embodiment. Also in the second embodiment, the bent portion of the meandering channel 232 which forms the resistance fluidic channel 26 is bent into an almost arcuate shape, but may be bent at an almost right angle, similar to the first embodiment.

In both the first and second embodiments, the resistance fluidic channel is arranged but may be omitted. The shape of the resistance fluidic channel 15, i.e., that of the meandering channel 132 is not limited to the above-mentioned crank shape and can be freely set.

In the first and second embodiments, the ends of the projections 133a and 233a formed in the cavities 133 and 233 contact the sheet-like members 12 and 22, respectively, but may be formed not to contact the sheet-like members. The internal capacities of the suction pumps 18 and 27 are increased by an amount by which the projections 133a and 233a are shortened, so the capacities of the suction pumps 18 and 27 can be increased. Since the ends of the projections 133a and 233a and portions of the sheet-like members 12 and 22 that are in contact with these ends are exposed, a large surface area can be ensured and in some cases, the surface area can be further increased, further increasing the suction force. For example, when a sample solution containing an impurity, such as food and drink or a body fluid, is injected into the flow cell, the inside of the suction pump 18 or 27 may be clogged with the impurity in a conventional structure. However, since the ends of the projections 133a and 233a do not contact the sheet-like members 12 and 22, respectively, gaps are formed between them, as described above. The impurity can pass through the gaps, preventing clogging of the insides of the suction pumps 18 and 27 with the impurity.

In the first to third embodiments, the slits 121, 221, and 321 have an almost rectangular shape when viewed from the top, and are formed at almost the centers of the sheet-like members 12, 22, and 32. However, the shapes and formation positions of the slits 121, 221, and 321 are not limited to them and can be freely set as long as the slits 121, 221, and 321 pass above the Au layers 11a, 21a, and 31a. The shapes and positions of the measurement fluidic channels 17, 25, and 35 defined by the slits 121, 221, and 321 can also be freely set.

In the first to third embodiments, the openings 122, 222, and 322 have an almost circular shape when viewed from the top. However, the shapes of the openings 122, 222, and 322 are not limited to this and can be freely set as long as the openings 122, 222, and 322 exist at positions where they are connected to the through holes 131, 231, and 331 of the second substrates 12, 23, and 33.

In the first embodiment, the cavity 133 has an almost U shape when viewed from the top. However, the planar shape of the cavity 133 is not limited to this and can be freely set. Similarly, in the second and third embodiments, the cavity 233 has an almost rectangular shape when viewed from the top. However, the planar shape of the cavity 233 is not limited to this and can be freely set. Further, the shapes of the projections 133a and 233a formed in the cavities 133 and 233 are not limited to an almost columnar shape and can be freely set as long as the surface areas in the cavities 133 and 233 increase.

In the first to fifth embodiments, the suction pump has a structure in which projections or channels are formed in a cavity or a structure in which a plurality of through holes are formed. However, the suction pump can adopt various kinds of structures as long as it sucks a liquid by the surface tension. For example, absorbent cotton may be disposed in the cavity to suck a liquid by the capillary force of the absorbent cotton. It is also possible to fill the inside of the cavity with fine particles such as microbead or zeolite, and suck a liquid by a capillary force generated in the space between adjacent fine particles. The inside of the slit 332a in the third embodiment or that of the through hole 57 in the fifth embodiment may be filled with absorbent cotton.

INDUSTRIAL APPLICABILITY

The flow cell is applicable to a field where a sample solution is handled, including micro-TAS, Lab-on-a-chip, micro combinatorial chemistry, chemical IC, chemical sensor, biosensor, microanalysis, electrochemical analysis, chromatography, QCM measurement, SPR measurement, and ATR measurement.

The invention claimed is:

1. A flow cell comprising:
   a plate-like member which includes a first substrate, a sheet-like member and a second substrate;
   an inlet port which is formed in said plate-like member and used to supply a liquid;
   a fluidic channel which is formed in said plate-like member and has one end connected to the inlet port; and
   a pump which is formed in said plate-like member, connected to the other end of the fluidic channel, and sucks, by a surface tension, the liquid flowing from the inlet port through the fluidic channel, wherein the fluidic channel is formed adjacent to a center of said plate-like member, and said pump is formed around the fluidic channel, except for a side of said one end on which the inlet port is formed, and
   wherein the pump is substantially U-shaped.

2. A flow cell according to claim 1, wherein said pump includes a cavity which is formed in said plate-like member, and a plurality of pillars which are formed in the cavity in a direction perpendicular to the fluidic channel.

3. A flow cell according to claim 1, wherein said pump includes a suction fluidic channel which is formed in said plate-like member and connected to the other end of the fluidic channel, and a plurality of connection holes which are formed in said plate-like member and connect the suction fluidic channel to an exterior portion of said pump.

4. A flow cell comprising:
   a plate-like member which includes a first substrate, a sheet-like member and a second substrate;
   an inlet port which is formed in said plate-like member and used to supply a liquid;
   a fluidic channel which is formed in said plate-like member and has one end connected to the inlet port; and
   a pump which is formed in said plate-like member, connected to the other end of the fluidic channel, and sucks, by a surface tension, the liquid flowing from the inlet port through the fluidic channel, wherein the fluidic channel is formed adjacent to a center of said plate-like member, and said pump is formed around the fluidic channel,
   wherein said pump is formed in parallel on either side of an axis of the fluidic channel extending axially from a vicinity of one end of the plate-like member to a vicinity of the other end thereof.

5. A flow cell according to claim 4, wherein said pump includes a cavity which is formed in said plate-like member, and a plurality of pillars which are formed in the cavity in a direction perpendicular to the fluidic channel.

6. A flow cell according to claim 4, wherein said pump includes a suction fluidic channel which is formed in said plate-like member and connected to the other end of the fluidic channel, and a plurality of connection holes which are formed in said plate-like member and connect the suction fluidic channel to an exterior portion of said pump.

7. A flow cell comprising:
   a plate-like member which includes a first substrate, a sheet-like member and a second substrate;
   an inlet port which is formed in said plate-like member and used to supply a liquid;
   a fluidic channel which is formed in said plate-like member and has one end connected to the inlet port; and
   a pump which is formed in said plate-like member, connected to the other end of the fluidic channel, and sucks, by a surface tension, the liquid flowing from the inlet port through the fluidic channel, wherein the fluidic channel is formed adjacent to a center of said plate-like member, and said pump is formed around the fluidic channel,
   wherein said pump includes a suction fluidic channel which is formed in said plate-like member and connected to the other end of the fluidic channel, and a plurality of connection holes which are formed in said plate-like member and connect the suction fluidic channel to an exterior portion of said pump.

8. A flow cell according to claim 7, wherein said pump is formed around the fluidic channel except for a side of said one end on which the inlet port is formed.

9. A flow cell according to claim 7, wherein said pump is formed on two sides of the fluidic channel in a direction perpendicular to a direction in which the fluidic channel extends.

* * * * *